(12) United States Patent
Bornstein

(10) Patent No.: US 6,582,681 B1
(45) Date of Patent: *Jun. 24, 2003

(54) METHOD AND A PREPARATION FOR CLEANING TOOTH ROOT SURFACES AND SURROUNDING TISSUE

(75) Inventor: Rolf Bornstein, Stockholm (SE)

(73) Assignee: Mediteam Dentalutveckling I Goteborg AB, Savedalen (SE)

( * ) Notice: Subject to any disclaimer, the term of this patent is extended or adjusted under 35 U.S.C. 154(b) by 0 days.

This patent is subject to a terminal disclaimer.

(21) Appl. No.: 09/857,425
(22) PCT Filed: Jul. 16, 1999
(86) PCT No.: PCT/SE99/01279
§ 371 (c)(1), (2), (4) Date: Jun. 4, 2001
(87) PCT Pub. No.: WO00/09077
PCT Pub. Date: Feb. 24, 2000

(30) Foreign Application Priority Data

Aug. 17, 1998 (SE) .............................................. 9802738

(51) Int. Cl.$^7$ .......................... A61K 7/20; C11D 3/395; C01B 11/06
(52) U.S. Cl. .................. 424/53; 510/369; 510/379; 510/383; 510/389; 252/186.25; 252/187.25; 252/187.26
(58) Field of Search ..................................... 424/49–58

(56) References Cited

U.S. PATENT DOCUMENTS

| | | | | |
|---|---|---|---|---|
| 3,684,722 A | * | 8/1972 | Hynam et al. | 252/98 |
| 3,903,252 A | * | 9/1975 | Steprns et al. | 424/49 |
| 3,956,158 A | * | 5/1976 | Donaldson | 252/102 |
| 4,271,030 A | * | 6/1981 | Brierley et al. | 252/88 |
| 4,585,570 A | * | 4/1986 | Nelson | 252/102 |
| 5,026,523 A | * | 6/1991 | Taya | 422/16 |
| 5,688,756 A | * | 11/1997 | Garabedian et al. | 510/369 |
| 5,697,985 A | * | 12/1997 | Good et al. | 8/528 |
| 5,827,810 A | * | 10/1998 | Brodbeck et al. | 510/369 |
| 5,851,421 A | * | 12/1998 | Choy et al. | 252/187.26 |
| 5,997,764 A | * | 12/1999 | Ambuter et al. | 252/186.25 |
| 6,017,515 A | * | 1/2000 | Van Den Bosch | 424/53 |
| 6,083,422 A | * | 7/2000 | Ambuter et al. | 252/187.26 |
| 6,099,310 A | * | 8/2000 | Bornstein et al. | 433/141 |
| 6,100,228 A | * | 8/2000 | Argo et al. | 510/379 |

FOREIGN PATENT DOCUMENTS

| | | |
|---|---|---|
| EP | 0 398 893 B1 | 11/1990 |
| EP | 398893 | * 10/1993 |
| SE | 460258 | * 9/1989 |
| WO | WO 97/19597 | 6/1997 |
| WO | 97/19597 | * 6/1997 |
| WO | WO 98/20838 | 5/1998 |
| WO | 98/20838 | * 5/1998 |
| WO | WO 99/34765 | 7/1999 |
| WO | 99/37465 | * 7/1999 |
| WO | 00/42974 | * 7/2000 |

* cited by examiner

*Primary Examiner*—Shep Rose
(74) *Attorney, Agent, or Firm*—Connolly Bove Lodge & Hutz LLP

(57) ABSTRACT

The invention relates to a method and a preparation for cleaning tooth root surfaces and surrounding tissue (periodontal pockets). The preparation is a two-component liquid of the type that has previously been used for chemical-mechanical treatment of carious lesion. The active component in the liquid is a hypochlorite, preferably sodium hypochlorite, and the other component in the liquid is a component which reduces the aggressiveness of the hypochlorite on healthy tissue and which also increases the viscosity of the liquid. The preparation is applied on the tooth root surface in question by means of a brush or an applicator instrument. After 10–15 seconds the root surface is cleaned by means of a scraping instrument.

10 Claims, No Drawings

METHOD AND A PREPARATION FOR CLEANING TOOTH ROOT SURFACES AND SURROUNDING TISSUE

The present invention relates to a method for cleaning tooth root surfaces and surrounding gingival tissue by means of a preparation which is applied on the root surface and in the periodontal pocket formed in the gingival tissue.

The tooth root is that part of the tooth which does not belong to the crown and which is normally enclosed within the gingival tissue and the jaw bone. Loss of teeth due to periodontal disease is together with caries one of our most frequent dental diseases, caused by a bacterial inflammatory activity starting from a plaque layer formed on the tooth surface and in the periodontal pocket.

If left unchecked the periodontal disease is gradually degenerating the bone support of the tooth and eventually causes loss of the tooth. In that case the process has been going on so long that most of the supporting structure surrounding the tooth has been lost. If the surrounding gingival tissue is not attached to the tooth, it does not contribute to the support of the tooth but merely makes the cleaning of the tooth more difficult and thereby increases dental calculus formation. The presence of dental calculus and the fact that the tooth root surface is not protected by any dental enamel may cause a bacterial activity and a further erosion of the jawbone.

The normal treatment method for gingivitis, ie inflammatory condition of the gingival tissue, and periodontal disease, is removal of plaque layers and calculus formations on the tooth root surfaces. Such a therapy must be followed by a very careful hygiene, specifically with respect to the tooth root surface at the gingival margin area in order to prevent any further inflammations. In case of very deep periodontal pockets, and when normal depuration and hygien has not been succesful, surgical periodontal therapy might be used, ie the gingival tissue is opened and calculus material, inflammatory tissue and degenerated jaw bone material is removed. Some times antibiotics and anti-bacterial pharmaceuticals can be used, specifically after a surgical operation during the healing period of the gingival tissue, for instance by means of a local antibiotical therapy with Elyzol in the periodontal pocket.

In some cases it is possible to reshape bone tissue to some extent. By modern bone-reshaping methods bone growth may be stimulated close to the tooth root, for instance by means of Emdogain or by means of specific filters or membranes (GTR).

For all these treatment methods a careful cleaning of the tooth root surface and the periodontal pocket is a critical factor. The cleaning can be done in connection with normal plaque and dental calculus removal (depuration) or in connection with surgical periodontal operations. The preparations that have been used so far in connection with cleaning of tooth root surfaces and periodontal pockets are usually not effective enough or they are too aggressive to healthy tissue. Cleaning liquids are difficult to apply on the infected tooth root surface, the liquid dissipates into periodontal pockets in the surrounding gingival tissue and there is a lot of waste and the cleaning procedure is often time-consuming. The cleaning liquid is not efficient enough when cleaning deep into the pockets is required. On the other hand liquids including more aggressive and efficient active components can not be used due to the risk of irritating the surrounding gum tissue.

To combine these methods with antibiotics is not to recommend, because of the systemic effect of the antibiotics and also because of the necessary repeatment of such an antibiotical treatment. Furthermore, doubtful long run results together with a certain resistence do not speek for antibiotic treatment methods.

The object of this invention is to provide a method and a preparation for cleaning tooth root surfaces and periodontal pockets and which solves the aforementioned problems. According to the invention a preparation of the type which has previously been used for chemical-mechanical treatment of caries, and in which the active component is a hypochlorite, preferably sodium hypochlorite, is used.

Such a preparation in the form of a two component liquid is described in SE 460258. The liquid is mixed immediately before treatment and is then applied to the caries cavity. Functioning in a biological way, the liquid makes the caries attacked substance soft without causing any damage to the tooth or the gum tissue. After 10–15 seconds the dentist can start removing the softened carious substance by scraping. The scraping operation continues until all carious substance has been removed. Then the cavity is filled with a suitable filling material.

In order to facilitate the handling of such a carious dissolving liquid it is previously known to include in the liquid a viscosity increasing substance (gel substance) and a coloring agent, see SE 507437. The gel substance is preferably a substance which has a reducing effect on the aggressiveness of the sodium hypochlorite on mucous membranes, preferably a carboxy methyl cellulose, and the coloring agent should have the ability to interact with carious tooth substance.

The component which is mixed with the sodium hypochlorite could be a component which consists of specific amino acids, but it can also consist of a gel component comprising a gel substance without any amino acids or a gel substance mixed with one or more amino acids, see Swedish patent application 9800025-0.

A common feature for these two-component liquids is the fact that they so far have been used only for caries treatment in tooth cavities.

However, it has now turned out quite unexpectedly that such a caries-dissolving liquid, which is previously known per se, can be used for cleaning tooth root surfaces and periodontal pockets. The active component in the liquid, the sodium hypochlorite, has not only a strong dissolving influence on degenerative collagen, but also has an anti-microbial effect.

The gel substance in the liquid reduces the aggressive influence of the hypochlorite on mucous membranes and the increased viscosity makes it more easy to apply the liquid on the tooth root and in the periodontal pocket. The liquid does not so easily spread itself outside the application site and the risk for spillage is reduced. Similar to the carious treatment method the gel component (amino acids) is added immediately before treatment.

In the following an example of a suitable preparation for cleaning tooth root surfaces and periodontal pockets will be described more in detail.

According to the invention the preparation consists of a hypochlorite component, preferably sodium hypochlorite, which has an anti-microbial effect, and a gel component. Which, when mixed with the sodium hypochlorite component, interacts with the component so that compounds are formed, which does not show the aggressiveness of sodium hypochlorite towards healthy gum tissue, but which maintains the dissolving effect on denaturated collagen as well as its anti-microbial effect.

In case of any early carious attacks on the root surfaces the caries is dissolved in the same way as in the "normal" use of the caries-dissolving liquid. Softened, infected and/or caries attacked tooth material is removed by scraping the tooth root surface by means of a scraping instrument such as the instrument illustrated in SE 9604626-3.

The gel substance component consists for instance of 2–10% carboxy methyle cellulose which concentration is sufficient for the gel substance alone to reduce the aggressive influence of the sodium hypochlorite on mucous membranes. Preferably a coloring agent is added to the gel substance in order to make the liquid and existing plaque on the tooth root surface more visible.

As mentioned in the introduction the two component liquid of this type is previously known per se, but used for another purpose, and the liquid itself will therefore not be described in any detail here. An example of a suitable liquid is Carisolv® marketed by MediTeam Dentalutveckling i Göteborg AB for chemical-mechanical treatment of caries.

When the liquid is used for cleaning the tooth root surfaces preferably small amounts of cleaning agents should be added to the liquid, such as EDTA (ethylene diamine tetraacetic acid) or citric acid.

The cleaning procedure of tooth root surfaces and periodontal pockets includes mixing of the liquid immediately before treatment and then applying the mixed liquid on the tooth root surface and in the periodontal pocket by means of a suitable applicator instrument, like the instrument used for caries treatment, or by means of a brush. After 10–15 seconds the dentist/dental hygienist starts cleaning the tooth root surface.

Thanks to the gel substance the liquid is not spread-out so easily, but is retained in the infected periodontal pocket and on the root surface. Compared to the caries treatment, in which case the liquid is applied into a tooth cavity, the tooth root surface is comparatively plane and therefore any suitable bonding agent should be included into the liquid, for instance of the type Sorbitol or Xylitol, so that the liquid is retained on the surface long enough.

The gel substance makes it also more easy for scraping with existing depuration instruments (dental calculus removal instruments) and furthermore reduces any pain feelings, compare shaving gel and razor, and probably depending on the reduced friction when the instrument engages the tooth root surface, without any cutting action, and a high pH-value.

The preparation has an astringent effect which reduces any tendency to bleeding during the cleaning, which makes it more easy to inspect the treated area which in turn makes the treatment more rapid.

By adding a coloring agent with the ability to interact with carious dentine, such as Erythrosin which is one of the ingredients in Carisolv®, early carious lesions on the tooth root surface could be more easily discovered and also treated in connection with the cleaning procedure. The coloring agent makes plaque/dental calculus visible and then it is easier to determine if the root surface is clean or not. The advantage by using a liquid like Carisolv® is that only denaturated collagen is dissolved, while healthy dentine and collagen in the mucous membrane are unaffected.

The invention is not limited to the above examples but can be varied within the scope of the accompanying claims.

What is claimed is:

1. A method for cleaning tooth root surfaces and surrounding tissue by means of a preparation which is applied on the tooth root surface to be cleaned and which comprises a hypochlorite, wherein said preparation is applied in the form of a two component liquid of the type used for chemical-mechanical treatment of carious lesion and in which the active component comprises said hypochlorite and the other component in the liquid is a gel component which, in addition to its ability to increase the viscosity and reduce the aggressivity of the hypochlorite to healthy tissue, has the ability to maintain the anti-microbial effect of the hypochlorite.

2. A method according to claim 2 characterized in that the liquid is applied on the root surface by means of an applicator instrument.

3. A method according to claim 3 characterized in that the liquid is applied on the root surface by brushing.

4. A preparation for cleaning tooth root surfaces and surrounding tissue comprising a hypochlorite, wherein said two-component liquid is of the type used for chemical-mechanical treatment of carious lesion and in which the active component comprises said hypochlorite, and the other component in the liquid is a gel component which, in addition to its ability to increase the viscosity and reduce the aggressivity of the hypochlorite to healthy tissue, has the ability to maintain the anti-microbial effect of the hypochlorite.

5. A preparation according to claim 4 characterized in the gel component consists of a gel substance with or without amino acids.

6. A preparation according to claim 5 characterized in that the gel component has an EDTA and/or citric acid additive.

7. A preparation according to claim 5 further comprising a bonding agent.

8. A preparation according to claim 7, wherein said bonding agent is selected from the group consisting of sorbitol and xylitol.

9. A method for cleaning tooth root surfaces and surrounding tissue according to claim 1 wherein said hypochlorite is sodium hypochlorite.

10. A preparation for cleaning tooth root surfaces and surrounding tissue according to claim 4 wherein said hypochlorite is sodium hypochlorite.

* * * * *